(12) United States Patent
Zemenchik et al.

(10) Patent No.: US 11,985,913 B2
(45) Date of Patent: May 21, 2024

(54) SOIL MONITORING SYSTEM

(71) Applicant: CNH Industrial America LLC, New Holland, PA (US)

(72) Inventors: Robert A. Zemenchik, Fair Oaks, CA (US); James Wayne Henry, Saskatoon (CA)

(73) Assignee: CNH Industrial America LLC, New Holland, PA (US)

( * ) Notice: Subject to any disclaimer, the term of this patent is extended or adjusted under 35 U.S.C. 154(b) by 608 days.

(21) Appl. No.: 17/245,604

(22) Filed: Apr. 30, 2021

(65) Prior Publication Data
US 2021/0259149 A1 Aug. 26, 2021

Related U.S. Application Data

(63) Continuation-in-part of application No. 15/499,210, filed on Apr. 27, 2017, now Pat. No. 11,064,642.

(51) Int. Cl.
*A01B 79/00* (2006.01)
*A01B 63/00* (2006.01)
(Continued)

(52) U.S. Cl.
CPC .......... *A01B 79/005* (2013.01); *A01B 63/008* (2013.01); *A01B 79/02* (2013.01);
(Continued)

(58) Field of Classification Search
CPC ..... A01B 79/005; A01B 63/008; A01B 79/02; A01C 21/007; G01N 21/84; G01N 33/24; G01N 2033/245; G01N 21/85
See application file for complete search history.

(56) References Cited

U.S. PATENT DOCUMENTS 5,033,397 A   7/1991   Colburn, Jr.
5,044,756 A   9/1991   Gaultney et al.
(Continued)

FOREIGN PATENT DOCUMENTS

CA   2640137   8/2007
RU   2329645   6/2007
(Continued)

OTHER PUBLICATIONS

EP Application No. 18167587.7 Extended European Search Report dated Sep. 28, 2018, 7 pgs.

*Primary Examiner* — Richard M Camby
(74) *Attorney, Agent, or Firm* — Rebecca L. Henkel; Rickard K. DeMille; Peter K. Zacharias (57) ABSTRACT

A soil monitoring system includes a controller having a memory and a processor. The controller is configured to instruct an actuator to drive a shank to move upwardly and downwardly, such that at least one soil monitoring sensor coupled to a lateral side of the shank moves in a cyclical pattern through soil as the shank is driven to move through the soil along a direction of travel. The controller is also configured to receive multiple sensor signals from the at least one soil monitoring sensor while the at least one soil monitoring sensor is at respective depths within the soil, in which each sensor signal is indicative of at least one soil property. In addition, the controller is configured to determine a vertical profile of the at least one soil property based on the sensor signals.

20 Claims, 6 Drawing Sheets

(51) Int. Cl.
- *A01B 79/02* (2006.01)
- *A01C 21/00* (2006.01)
- *G01N 21/84* (2006.01)
- *G01N 33/24* (2006.01)

(52) U.S. Cl.
CPC .......... *A01C 21/007* (2013.01); *G01N 21/84* (2013.01); *G01N 33/24* (2013.01); *G01N 2033/245* (2013.01)

(56) References Cited

U.S. PATENT DOCUMENTS

| | | | |
|---|---|---|---|
| 5,461,229 A | 10/1995 | Sauter et al. | |
| 5,524,560 A | 6/1996 | Carter | |
| 6,356,830 B1 | 3/2002 | Adamchuck et al. | |
| 6,484,652 B1 | 11/2002 | Colburn, Jr. | |
| 6,853,937 B2 | 2/2005 | Shibusawa et al. | |
| 8,827,001 B2 | 9/2014 | Wendte et al. | |
| 8,862,339 B2 | 10/2014 | Henry et al. | |
| 11,882,782 B2 * | 1/2024 | Sloneker | A01C 5/064 |
| 2003/0009286 A1 | 1/2003 | Shibusawa et al. | |
| 2003/0016029 A1 | 1/2003 | Schuler et al. | |
| 2005/0172733 A1 | 8/2005 | Drummond et al. | |
| 2011/0106451 A1 | 5/2011 | Christy et al. | |
| 2015/0323491 A1 | 11/2015 | Miller et al. | |
| 2015/0366125 A1 | 12/2015 | Cross et al. | |
| 2017/0094889 A1 | 4/2017 | Garner et al. | |
| 2018/0310456 A1 | 11/2018 | Zemenchik et al. | |
| 2023/0263088 A1 * | 8/2023 | Koch | A01B 47/00 172/4 |
| 2023/0417725 A1 * | 12/2023 | Stoller | G01N 33/24 |

FOREIGN PATENT DOCUMENTS

| | | |
|---|---|---|
| WO | 2006015463 | 2/2006 |
| WO | 2016205422 | 12/2016 |

* cited by examiner

SOIL MONITORING SYSTEM

CROSS-REFERENCE TO RELATED APPLICATION

The present application is a continuation-in-part of U.S. patent application Ser. No. 15/499,210, entitled "AGRICULTURAL SHANK WITH PROTECTED SOIL SENSOR", filed Apr. 27, 2017, which is hereby incorporated by reference in its entirety.

BACKGROUND

The present disclosure relates to agricultural implements, and, more particularly, to agricultural implements which carry shanks.

Farmers utilize a wide variety of implements including tillage implements to prepare soil for planting and planting implements for the planting of seeds. Some such implements include two or more sections coupled together to perform multiple functions as they are pulled through fields by a tractor. For example, a field cultivator is capable of simultaneously tilling soil and leveling the tilled soil in preparation for planting. A field cultivator has a frame that carries a number of cultivator shanks with shovels at their lower ends for tilling the soil. The field cultivator converts compacted soil into a level seedbed with a consistent depth for providing excellent conditions for planting of a crop. Grass or residual crop material disposed on top of the soil is also worked into the seedbed so that it does not interfere with a seeding implement subsequently passing through the seedbed.

Other agricultural implements that also carry shanks are fertilizer applicators and sub-soilers. Fertilizer applicators can carry shanks which prepare the soil to receive solid, liquid, and/or gaseous fertilizer to increase plant yield in a field. Typically, the shanks carried by fertilizer applicators do not penetrate too deeply into the soil. Sub-soilers, on the other hand, can carry shanks which extend deep into the soil in order to break up a compaction layer, which is also referred to as a hardpan, to allow greater root penetration by the crops. Shanks carried by agricultural implements, therefore, provide various functionalities to the implement depending upon the configuration of the shanks.

One particular challenge of agronomy that has remained unsolved is reliably and conveniently quantifying the form of nitrogen, nitrate-N, which is available in the soil for plant root uptake. One way to determine soil nitrate-N concentration, which can also be referred to as a nitrate-N level, is by subjecting multiple soil samples from a field to various chemical tests in a laboratory environment. While such laboratory chemical tests can be accurate for the specific soil samples tested, the levels of nitrate-N throughout a field can be drastically different depending on the local soil conditions. Further, testing soil samples at a laboratory remote from the field does not provide a farmer with the levels of nitrate-N in the soil samples until days, possibly even weeks, after the soil samples are collected. Thus, the farmer has only limited, possibly unreliable, information to utilize when determining how to dispense fertilizer to the field which can result in the nitrate-N levels being too low in one part of the field, reducing potential yield, and too high in another part of the field, wasting fertilizer and/or possibly raising the nitrate-N levels to uneconomical levels.

BRIEF DESCRIPTION

In certain embodiments, a soil monitoring system includes a controller having a memory and a processor. The controller is configured to instruct an actuator to drive a shank to move upwardly and downwardly, such that at least one soil monitoring sensor coupled to a lateral side of the shank moves in a cyclical pattern through soil as the shank is driven to move through the soil along a direction of travel. The controller is also configured to receive multiple sensor signals from the at least one soil monitoring sensor while the at least one soil monitoring sensor is at respective depths within the soil, in which each sensor signal is indicative of at least one soil property. In addition, the controller is configured to determine a vertical profile of the at least one soil property based on the sensor signals.

DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

One or more specific embodiments of the present disclosure will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of operating parameters and/or environmental conditions are not exclusive of other parameters/conditions of the disclosed embodiments.

Figure 1:
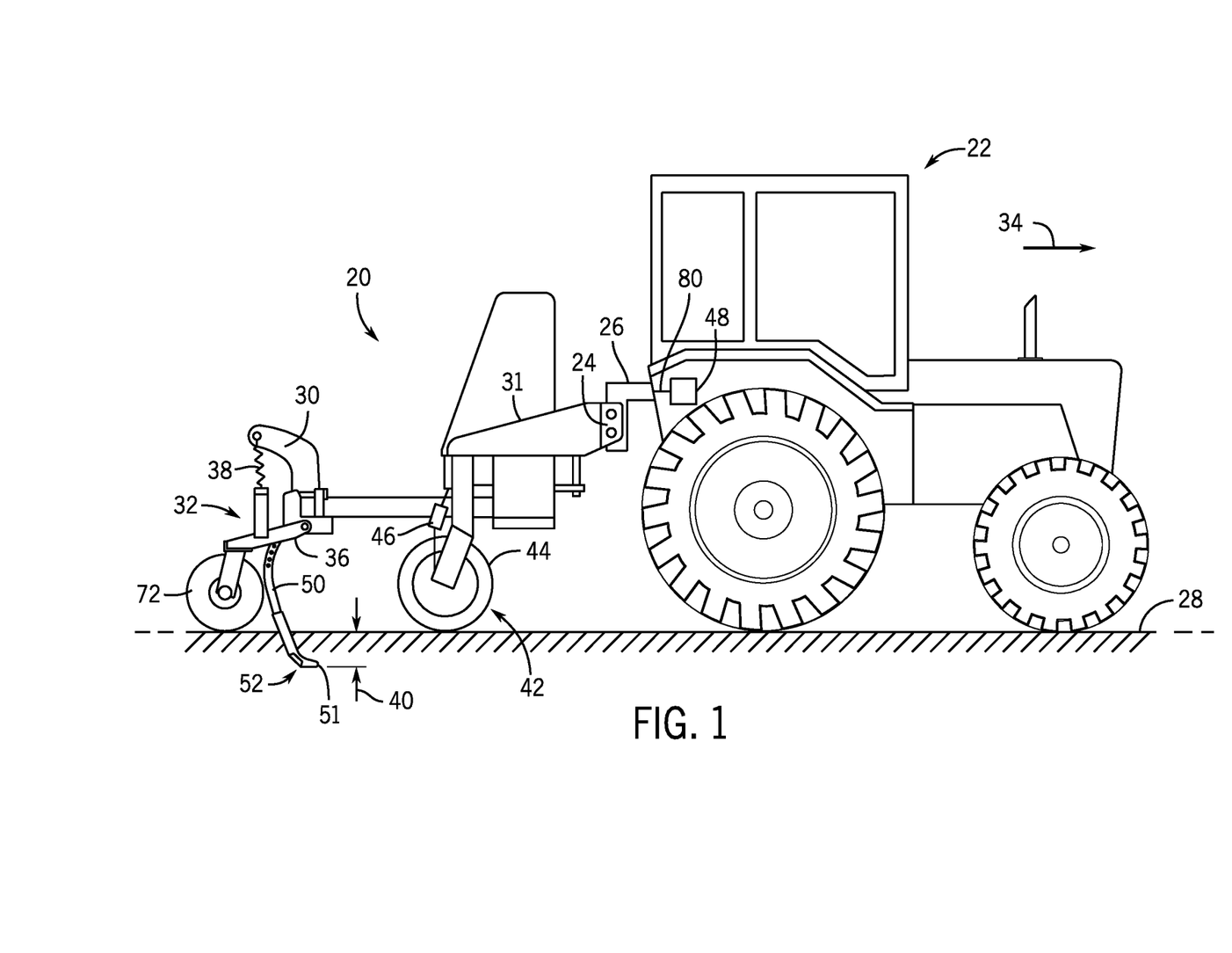
FIG. 1 is a side view of an embodiment of an agricultural implement.

Referring now to the drawings, and more particularly to FIG. 1, an embodiment of an agricultural implement 20 is shown. The implement 20 is designed to be towed behind a work vehicle, such as the illustrated tractor 22, but it should be appreciated that the implement 20 can also be self-powered by an internal combustion engine or other power source if desired. In the illustrated embodiment, the implement 20 includes a hitch 24 configured to attach to an appropriate tractor hitch assembly 26. The tractor hitch assembly 26 may be adjustable to enable an operator and/or an automated system to vary a height of the implement 20 relative to a soil surface 28, which can also be referred to as a soil top surface, on which the tractor 22 and implement 20 are traveling. As illustrated, the hitch 24 is coupled to an implement frame 30 which is carried by a chassis 31 of the implement 20 and configured to support multiple tools, such as the illustrated shank 32. In this configuration, the shank 32 faces oncoming soil as the implement 20 is towed in a direction of travel 34, as will be further described herein. The shank 32 is supported by an arm 36, which is rotatably coupled to the frame 30. In the illustrated embodiment, a retractor 38 extends between the frame 30 and the arm 36. The retractor 38 is configured to vertically lift up (e.g., retract) the shank 32 if any portion of the shank 32 encounters an obstruction (e.g., a rock, tree root, etc.) which applies a resistive force to the shank 32 that exceeds a threshold resistive force, which can be adjusted as desired, thereby substantially protecting components of the shank 32. If desired, the retractor 38 can be configured to pull an entirety of the shank 32 vertically above the soil surface 28 immediately upon the shank 32 experiencing the threshold resistive force. The retractor 38 can be, for example, a spring, as shown, or a hydraulic accumulator commonly employed in European style agricultural implements, as is known.

In certain embodiments, a penetration depth 40 of up to 40 cm of the shank 32 may be adjusted as the implement 20 is pulled through the field for varying reasons. In such embodiments, the trailer hitch 26 may adjust a vertical position of the frame 30 relative to the tractor 22 to vary the penetration depth 40 of the shank 32 within a range of 0 cm to 40 cm deep. In addition, as the height of the frame 30 above the soil surface 28 varies, a wheel assembly 42 may adjust a vertical position of a gauge wheel 44 relative to the frame 30, thereby enabling the wheel assembly 42 to support the frame 30 throughout the range of vertical frame movement. For example, in the illustrated embodiment, the wheel assembly 42 includes an actuator 46 configured to adjust the vertical position of the gauge wheel 44 relative to the frame 30. As will be appreciated, the actuator 46 may be a linear actuator, such as a hydraulic cylinder, a pneumatic cylinder, or an electromechanical actuator, or a rotary actuator, such as a hydraulic servo or an electric servo. In this sense, the actuator 46 is configured to adjust the penetration depth 40 of the shank 32 within the range of 0 cm to 40 cm deep by adjusting the vertical position of the gauge wheel 44 relative to the frame 30, but it should be appreciated that a separate actuator can also be connected directly to the shank 32 to selectively adjust the penetration depth 40 of the shank 32 within the range of 0 cm to 40 cm deep. The actuator 46 can be electrically coupled to a controller 48 configured to control the actuator 46. The controller 48 can also be coupled to other components of the implement 20 to control operation of various aspects of the implement 20, which is discussed further herein.

Figure 2:
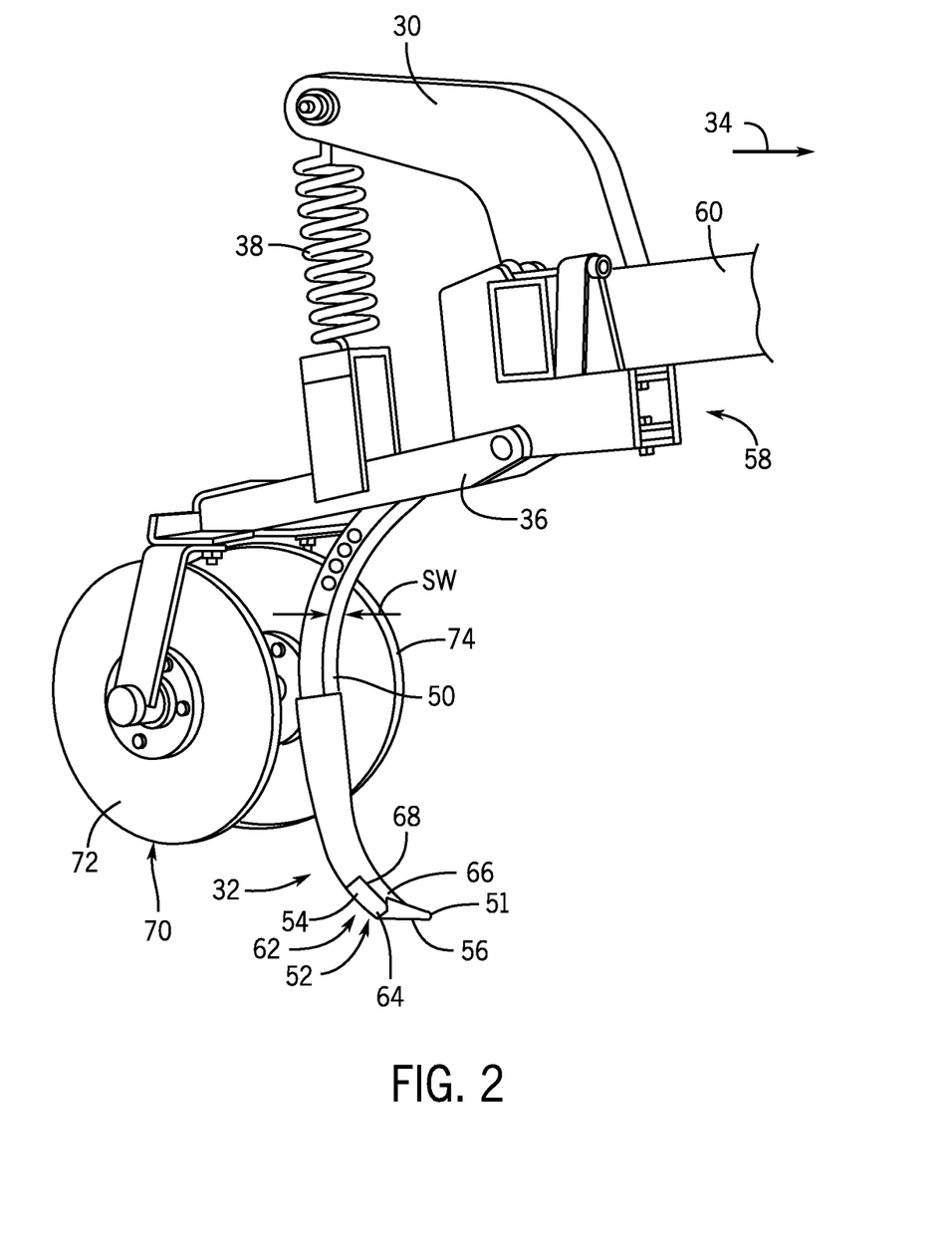
FIG. 2 is a perspective view of an embodiment of a shank.

Referring now to FIG. 2, a perspective view of an embodiment of a shank 32 is shown. The shank 32 includes a shank body 50 which is configured to partially or completely penetrate the soil surface, a sensor 52 attached to an outer surface 54 of the shank body 50, and a sensor shield 56 carried by the shank body 50 in front of the sensor 52. The shank 32 can connect to a mount 58 which can connect to a toolbar 60 carried by the chassis so the shank 32 travels in the travel direction 34 as the tractor pulls the implement across a field. The shank body 50 may have a generally curved structure descending down toward the soil surface during operation and may be affixed with a tillage point 51, as shown, or have any other suitable construction that allows the shank body 50 to penetrate the soil surface during operation of the implement. The shank body 50 can also have a generally rectangular cross-section with a shank width SW of approximately 0.75" to 2.0". It should be appreciated that the shape and size of the shank body 50 can be adjusted as desired in order to better carry out the functionality of the agricultural implement, whether the agricultural implement is a field cultivator, a fertilizer applicator, a subsoiler, etc.

The sensor 52 attached to the outer surface 54 of the shank body 50 defines a probing area 62 adjacent the sensor 52 in which the sensor 52 can effectively sense one or more desired parameters. For example, the sensor 52 can be configured as an optical nitrate-N sensor with a window 64 which allows a signal in the form of emitted energy, such as light, from the sensor to contact soil adjacent to the window 64 to facilitate determination of a concentration of nitrate-N in the soil within the probing area 62. In this sense, the exact size and shape of the probing area 62 depends upon the configuration of the sensor 52 and the desired sample size. An ionic chemical sensor, for example, may define a probing area at a tip of the sensor which contacts soil, whereas an optical sensor may define a probing area a certain distance away from a window of the sensor. It should thus be appreciated that various sensors define differing probing areas, depending upon the configuration of the sensor, which can be adjusted as desired to sense different parameters of soil adjacent to the sensor as the sensor is carried by the shank body 50.

The sensor shield 56 is carried by the shank body 50 in front of the sensor 52, relative to the travel direction 34, and is shaped in such a way that the sensor shield 56 deflects oncoming soil away from the sensor 52 without substantially disrupting soil flow into the probing area 62. As used herein, the sensor shield 56 does not "substantially disrupt soil flow into the probing area" so long as the sensor shield 56 does not move so much oncoming soil that the probing area 62 is devoid of sampleable soil as the implement travels in the travel direction 34 and drags the shank 32 and sensor 52 through soil. When the outer surface 54 to which the sensor 52 is attached is a lateral surface of the shank body 50 so the probing area 62 is adjacent a lateral side of the shank body 50, the sensor shield 56 can be shaped with a beveled surface 66 that extends laterally relative to the travel direction 34 so oncoming soil is directed laterally away from the sensor 52. The lateral surface 54 may thus define a lateral edge 68 of the shank body 50, with the beveled surface 66 of the sensor shield 56 extending laterally past the lateral edge 68 to direct oncoming soil away from the sensor 52. The beveled surface 66, which can also be referred to as a deflecting surface, can terminate immediately adjacent to the probing area 62 of the sensor 52 so re-directed soil is forced into the probing area 62, enabling the sensor 52 to analyze the soil. Rather than a flat, beveled surface, the deflecting surface 66 of the sensor shield 56 can be formed with a curvature to have a partial or full conical shape that enables the sensor shield 56 to direct soil away from the sensor 52 without substantially disrupting soil flow into the probing area 62. Thus, the sensor shield 56 can direct oncoming soil flow from colliding with parts of the sensor 52 while also enabling soil flow into the probing area 62 for analysis by the sensor 52.

As the shank 32 travels through soil, the displacement of soil by the shank 32 can cause a slot to form in the soil, which may be undesired. To help close the formed slot, the implement can include a closing device 70 carried behind the shank 32 and configured to at least partially close the formed slot caused by the shank 32 during travel through soil. The closing device 70 may include, for example, a pair of angled disc blades 72, 74 which are coupled to the same arm 36 to which the shank 32 attaches. While the closing device 70 is shown with a pair of disc blades 72, 74, many types of closing devices are known and the closing device 70 may be any suitable closing device.

Figure 3:
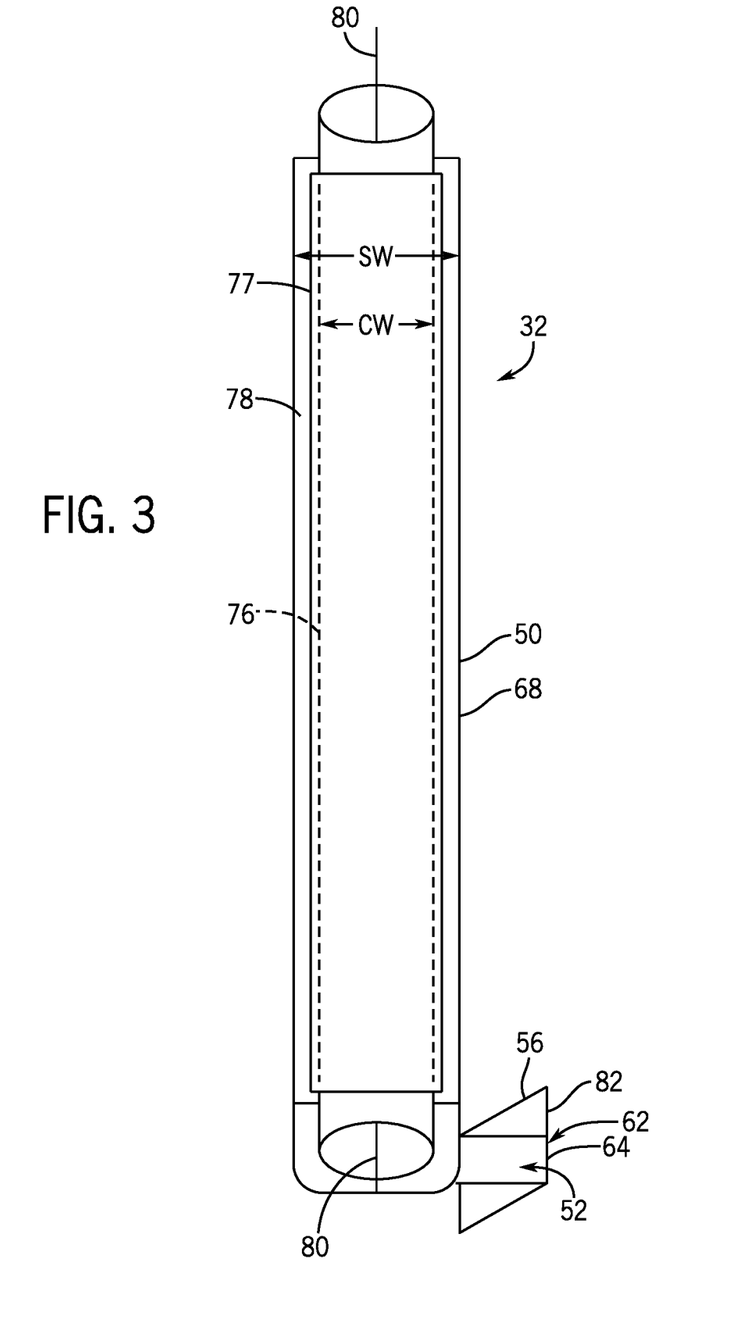
FIG. 3 is a rear view of the shank shown in FIG. 2.

Referring now to FIG. 3, a rear view of the shank 32 is shown so a conduit 76 attached to a rear surface 78 of the shank body 50 can be seen. The conduit 76, which can be formed as a metal or plastic tube, can house a wire 80 which couples the sensor 52 to the controller, allowing data acquired by the sensor 52 to be fed to the controller for processing, analysis, and/or subsequent control of other aspects of the implement by the controller, as well as enabling electrical power to be provided to the sensor 52 through the wire 80. While the sensor 52 is shown as being coupled to the controller by the wire 80, the sensor 52 can also be configured to transmit signals wirelessly to the controller and have a separate power source, such as a battery. The conduit 76 can be formed with a conduit width CW, or conduit diameter when the conduit 76 is round, which is no greater than the shank width SW of the shank body 50, which can enable the conduit 76 to protect the wire 80 without substantially contributing to slot formation in the soil as the shank 32 travels through the soil. If desired, the conduit 76 may also be rearwardly enclosed by another protective subassembly 77. As can also be seen, a lateral shield edge 82 of the sensor shield 56 can be flush with the window 64 of the sensor 52 so the sensor shield 56 can shield an entire front of the sensor 52 from oncoming soil and other objects, protecting the relatively delicate and expensive sensor 52 from impacts as the implement travels across a field.

Figure 4:
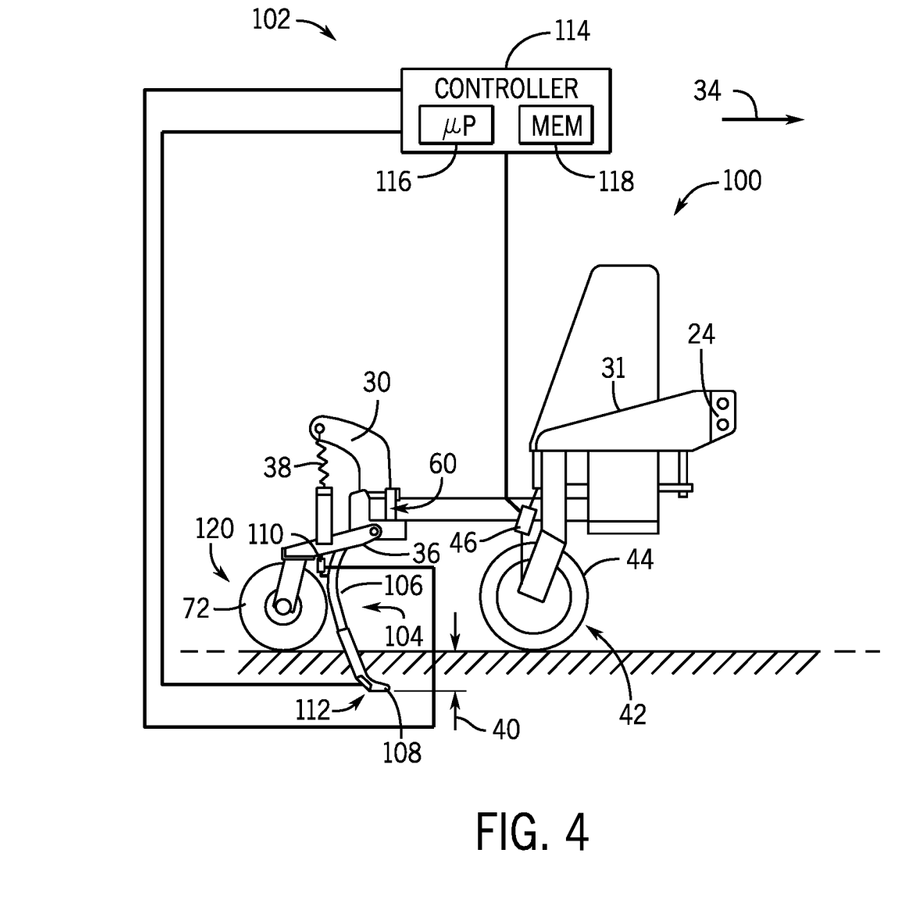
FIG. 4 is a side view of another embodiment of an agricultural implement, in which the agricultural implement includes an embodiment of a soil monitoring system.

FIG. 4 is a side view of another embodiment of an agricultural implement 100, in which the agricultural implement 100 includes an embodiment of a soil monitoring system 102. In the illustrated embodiment, the soil monitoring system 102 includes a shank 104 configured to engage soil. The shank 104 includes a body 106 and a tillage point 108 coupled to the body 106. As previously discussed, the shank 104 is supported by the arm 36, which is rotatably coupled to the frame 30. Furthermore, the wheel assembly 42 includes an actuator 46 configured to adjust the vertical position of the gauge wheel 44 relative to the frame 30, thereby controlling the penetration depth of each shank 104 coupled to the frame 30.

In the illustrated embodiment, the soil monitoring system 102 also includes an actuator 110 coupled to the shank 104 (e.g., one shank 104 of the agricultural implement 100) and configured to drive the shank 104 to move upwardly and downwardly relative to the frame 30. Accordingly, the wheel assembly actuator 46 may control the penetration depth of each shank coupled to the frame 30, and the shank actuator 110 may control the penetration depth of the respective shank 104 independently of the other shanks coupled to the frame 30. The shank actuator 110 may include any suitable type(s) of actuator(s), such as hydraulic actuator(s), pneumatic actuator(s), electromechanical actuator(s), other suitable type(s) of actuator(s), or a combination thereof. For example, in certain embodiments, the body 106 of the shank 104 may be coupled to the frame 30 by a sliding joint that enables the shank 104 to move upwardly and downwardly relative to the frame 30. In such embodiments, the shank actuator 110 may be coupled to the frame 30 and to the shank body 106 to control the position of the shank 104 relative to the frame 30, thereby varying the penetration depth of the respective tillage point 108. The shank actuator 110 may be configured to drive the shank 104 to move through any suitable range of motion. For example, the shank actuator 110 may be configured to drive the shank 104 to move upwardly and downwardly such that the penetration depth of the shank varies by at least 3 inches (e.g., 8 cm), by at least 4 inches (e.g., 10 cm), by at least 6 inches (e.g., 15 cm), by at least 9 inches (e.g., 23 cm), by at least 12 inches (e.g., 30 cm), by at least 14 inches (e.g., 36 cm), by at least 16 inches (e.g., 41 cm), by at least 18 inches (e.g., 46 cm), by at least 20 inches (e.g., 51 cm), or by at least 24 inches (e.g., 61 cm).

Furthermore, in the illustrated embodiment, the soil monitoring system 102 includes one or more soil monitoring sensors (e.g., optical soil monitoring sensors 112) coupled to a lateral side of the shank 104 (e.g., to a lateral side of the body 106 of the shank 104). As used herein, "lateral side" refers to a side of the shank extending at least partially along the direction of travel 34 (e.g., entirely along the direction of travel). Each optical soil monitoring sensor 112 is configured to output sensor signals indicative of at least one soil property. For example, the optical soil monitoring sensor(s) 112 may include an optical nitrate-N sensor. Furthermore, as discussed in detail below, the soil monitoring system 102 may include multiple optical soil monitoring sensors disposed along a vertical axis of the shank, thereby enabling the soil monitoring system to monitor one or more soil properties at different soil depths concurrently. In addition, in certain embodiments, the soil monitoring system 102 may include one or more second optical soil monitoring sensors coupled to a second lateral side of the shank 104, opposite the lateral side (e.g., first lateral side) of the shank.

In the illustrated embodiment, the soil monitoring system 102 includes a controller 114 (e.g., a controller coupled to the agricultural implement, a controller coupled to the work vehicle towing the agricultural implement, a controller of a remote control system, another suitable controller, or a combination thereof) communicatively coupled to the shank actuator 110 and to the optical soil monitoring sensor(s) 112. As discussed in detail below, the controller 114 is configured to control the actuator 110, to receive the sensor signals from each optical soil monitoring sensor 112 while the optical soil monitoring sensor is at respective depths within the soil, and to determine vertical profile(s) of the soil property/properties based on the sensor signals. In certain embodiments, the controller 114 is an electronic controller having electrical circuitry configured to determine the vertical profile(s) of the soil property/properties. In the illustrated embodiment, the controller 114 includes a processor, such as the illustrated microprocessor 116, and a memory device 118. The controller 114 may also include one or more storage devices and/or other suitable components. The processor 116 may be used to execute software, such as software for controlling the actuator 110 and/or for determining the vertical profile(s) of the soil property/properties, and so forth. Moreover, the processor 116 may include multiple microprocessors, one or more "general-purpose" microprocessors, one or more special-purpose microprocessors, and/or one or more application specific integrated circuits (ASICs), or some combination thereof. For example, the processor 116 may include one or more reduced instruction set (RISC) processors.

The memory device 118 may include a volatile memory, such as random access memory (RAM), and/or a nonvolatile memory, such as read-only memory (ROM). The memory device 118 may store a variety of information and may be used for various purposes. For example, the memory device 118 may store processor-executable instructions (e.g., firmware or software) for the processor 116 to execute, such as instructions for controlling the actuator 110 and/or for determining the vertical profile(s) of the soil property/properties, and so forth. The storage device(s) (e.g., non-volatile storage) may include ROM, flash memory, a hard drive, or any other suitable optical, magnetic, or solid-state storage medium, or a combination thereof. The storage device(s) may store data, instructions (e.g., software or firmware for controlling the actuator 110 and/or for determining the vertical profile(s) of the soil property/properties, etc.), and any other suitable data.

In certain embodiments, the controller 114 is configured to instruct the shank actuator 110 to drive the shank 104 to move upwardly and downwardly, such that the optical soil monitoring sensor(s) 112, which are coupled to the lateral side of the shank 104, move in a cyclical pattern through the soil as the shank 104 is driven to move through the soil along the direction of travel 34. In addition, the controller 114 is configured to receive the sensor signals from each optical soil monitoring sensor 112 indicative of the soil property/properties at respective depths within the soil. The controller 114 is also configured to determine vertical profile(s) of the soil property/properties based on the sensor signals. Furthermore, in certain embodiments, the controller is configured to control output of at least one agricultural product based on the vertical profile(s) of the soil property/properties. In addition, in certain embodiments, the controller is configured to control operation of a ground engaging tool coupled to the agricultural implement based on the vertical profile(s) of the soil property/properties. For example, in the illustrated embodiment, the controller 114 is communicatively coupled to the wheel assembly actuator 46. In certain embodiments, the controller 114 may control the wheel assembly actuator 46 to adjust the penetration depth of the shanks coupled to the frame 30 based on the vertical profile(s) of the soil property/properties. Furthermore, in certain embodiments, the controller may control a speed of the agricultural implement and/or a direction of movement of the agricultural implement based on the vertical profile(s) of the soil property/properties.

In the illustrated embodiment, the soil monitoring system 102 includes a closing assembly 120 configured to close a trench formed by the shank 104 (e.g., as compared to a trench formed by another tool of the agricultural implement). As illustrated, the closing assembly 120 includes at least one angled disc blade 72 (e.g., 1, 2, 3, 4, 5, 6, or more). However, in other embodiments, the closing assembly may include other suitable closing device(s) (e.g., alone or in combination with the angled disc blade(s)), such as one or more closing knives, other suitable type(s) of closing device(s), or a combination thereof. Furthermore, in certain embodiments, the closing assembly may be omitted. In addition, in the illustrated embodiment, the implement 100 includes the retractor 38, as discussed in detail above, extending between the frame 30 and the arm 36 that supports the shank 104. However, in other embodiments, the retractor may be omitted.

While the soil monitoring system 102 includes a single shank 104 supporting one or more optical soil monitoring sensors 112 in the illustrated embodiment, in other embodiments, the soil monitoring system may include multiple shanks, in which one or more optical soil monitoring sensors are coupled to the lateral side of each shank. In such embodiments, each optical soil monitoring sensor may be communicatively coupled to the controller and configured to output respective signal(s) indicative of one or more soil property/properties. In addition, an actuator may be coupled to each shank supporting one or more optical soil monitoring sensors, in which the actuator is configured to drive the shank to move upwardly and downwardly in response to instructions from the controller. In certain embodiments (e.g., in embodiments in which the optical soil monitoring sensor(s) coupled to one shank are positioned at different location(s) along the vertical extent of the shank than the optical soil monitoring sensor(s) of another shank), the controller may instruct the actuators to drive the shanks to move upwardly and downwardly together (e.g., in unison, in phase, etc.). However, in other embodiments (e.g., in embodiments in which the optical soil monitoring sensor(s) coupled to one shank are positioned at the same location(s) along the vertical extent of the shank as the optical soil monitoring sensor(s) of another shank), the controller may instruct at least two actuators to drive the respective shanks in different cyclical patterns (e.g., out of phase, not in unison, etc.). Furthermore, in certain embodiments, the soil monitoring system may include at least one shank supporting one or more optical soil monitoring sensors and non-movably coupled to the arm.

Furthermore, while the shank 104 is supported by the arm 36 in the illustrated embodiment, in other embodiments, shank(s) (e.g., movable shank(s), in which one or more optical soil monitoring sensors are coupled to the lateral side of each shank) may be movably coupled to any suitable structure of the agricultural implement, to any suitable structure of the work vehicle towing the agricultural implement, to any suitable structure of another agricultural implement towed by the work vehicle, to any suitable structure of another element/system coupled to the agricultural implement, or a combination thereof. For example, in certain embodiments, at least one shank (e.g., movable shank, in which one or more optical soil monitoring sensors are coupled to the lateral side of the shank) may be movably coupled to the hitch coupling the work vehicle and the agricultural implement, to the front of the work vehicle, or to the front of another agricultural implement towed by the work vehicle.

Figure 5:
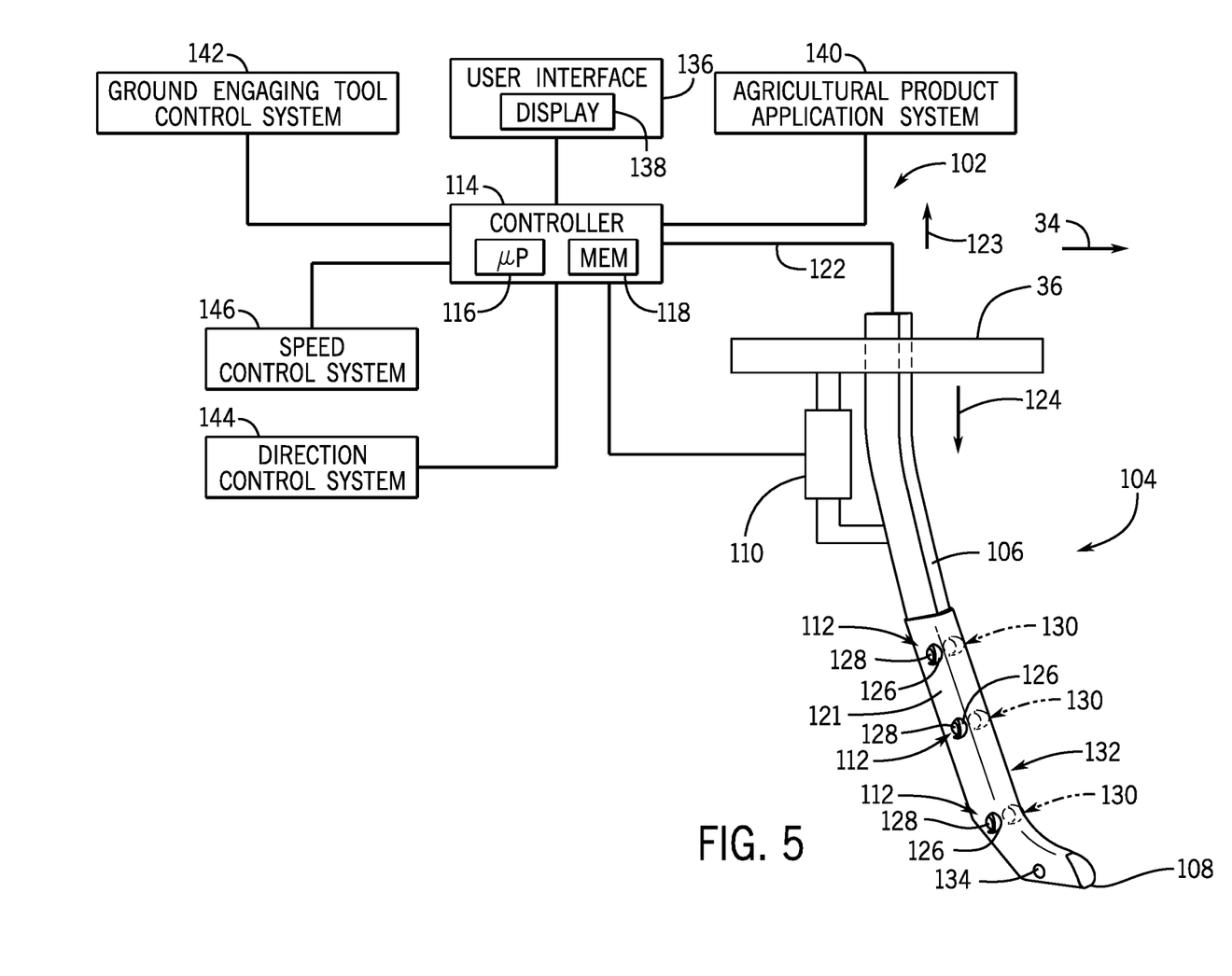
FIG. 5 is a perspective view of a portion of the soil monitoring system of FIG. 4.

FIG. 5 is a perspective view of a portion of the soil monitoring system 102 of FIG. 4. As previously discussed, the soil monitoring system 102 includes optical soil monitoring sensor(s) 112 coupled to a lateral side (e.g., first lateral side 121) of the shank 104 and communicatively coupled to the controller 114 (e.g., via a sensor connection 122). In certain embodiments, the sensor connection 122 includes one or more electrical conductors extending between the optical soil monitoring sensor(s) 112 and the controller 114. In such embodiments, the electrical conductor(s) may extend through a conduit attached to a rear surface of the shank body, as previously discussed above with regard to FIG. 3. Additionally or alternatively, the electrical conductor(s) may extend through a passage within the shank (e.g., within the shank body). Furthermore, in certain embodiments, any of the sensors disclosed herein may be communicatively coupled to the controller by a wireless connection.

In addition, the controller 114 is configured to instruct the shank actuator 110 to drive the shank 104 to move upwardly (e.g., in an upward direction 123) and downwardly (e.g., in a downward direction 124) relative to the soil surface as the shank 104 is driven to move through the soil along the direction of travel 34. Accordingly, the shank 104 is driven to move in a cyclical pattern through the soil. In addition, the controller 114 is configured to receive sensor signals from each optical soil monitoring sensor 112 while the optical soil monitoring sensor is at respective depths within the soil. For example, the controller may receive a respective sensor signal from each optical soil monitoring sensor 112 while the optical soil monitoring sensor is at a respective depth within the soil. The controller may receive the sensor signals at any suitable interval as the optical soil monitoring sensor(s) move through the soil. As previously discussed, each sensor signal is indicative of one or more soil properties. Furthermore, the controller 114 is configured to determine vertical profile(s) of the soil property/properties based on the sensor signals.

In certain embodiments, at least one optical soil monitoring sensor 112 includes an optical nitrate-N sensor. For example, in certain embodiments, each optical soil monitoring sensor 112 of the soil monitoring system 102 includes an optical nitrate-N sensor. Furthermore, in certain embodiments, at least one optical soil monitoring sensor 112 may include another suitable type of optical soil monitoring sensor configured to detect another soil property/other soil properties, such as organic composition, soil density, soil moisture content, other suitable soil property/properties, or a combination thereof.

In the illustrated embodiment, the soil monitoring system 102 includes three optical soil monitoring sensors 112 disposed along a vertical extent of the shank 104. Accordingly, as the shank moves through the soil along the direction of travel 34, each optical soil monitoring sensor outputs sensor signals indicative of soil property/properties at respective depths beneath the soil surface. As such, the soil monitoring system 102 may monitor the soil property/properties at multiple depths concurrently. In addition, because the soil monitoring system 102 includes multiple optical soil monitoring sensors 112 disposed along the vertical extent of the shank 104, the controller 114 may determine the vertical profile(s) of the soil property/properties via a smaller vertical movement of the shank 104 (e.g., as compared to a soil monitoring system having a single optical soil monitoring sensor coupled to the shank). While the soil monitoring system 102 includes three optical soil monitoring sensors 112 disposed along the vertical extent of the shank 104 in the illustrated embodiment, in other embodiments, the soil monitoring system may include more or fewer optical soil monitoring sensors disposed along the vertical extent of the shank (e.g., 1, 2, 4, 5, 6, or more).

In the illustrated embodiment, the soil monitoring system 102 includes bosses 126 extending laterally outward from the lateral side (e.g., the first lateral side 121) of the shank 104. Each boss 126 at least partially surrounds a portion of a respective optical soil monitoring sensor 112 (e.g., a window 128 of the respective optical soil monitoring sensor 112). In addition, each boss 126 is configured to direct soil around at least the portion (e.g., the window 128) of the respective optical soil monitoring sensor 112. For example, in the illustrated embodiment, each optical soil monitoring sensor 112 includes a window 128 extending laterally outward from the lateral side (e.g., the first lateral side 121) of the shank 104. Each boss 126 is positioned forward of the respective window 128 relative to the direction of travel 34. Accordingly, each boss 126 directs soil around the respective window 128 as the shank 104 moves along the direction of travel 34, thereby substantially blocking soil from contacting a forward-facing surface of the respective window 128. In certain embodiments, the maximum lateral extent of at least one window 128 is equal to the maximum lateral extent of the respective boss(es) 126, such that an outer lateral edge of each boss 126 is flush (e.g., substantially flush) with an outer lateral end of the respective window 128. Furthermore, each boss 126 is configured to direct oncoming soil flow into a probing area of the respective optical soil monitoring sensor 112 without substantially disrupting soil flow into the probing area, thereby enabling the respective optical soil monitoring sensor 112 to effectively monitor the soil property/properties at the probing area.

In the illustrated embodiment, each boss 126 has a substantially curved shape to match the curved shape of the respective window 128. However, in other embodiments, at least one boss may have another suitable shape (e.g., chevron shape, polygonal shape, etc.). For example, the boss may be shaped to match the shape of the window. Furthermore, while each boss 126 partially surrounds the respective window 128 in the illustrated embodiment, in other embodiments, at least one boss may completely surround the respective window. In addition, while each boss 126 contacts the respective window 128 in the illustrated embodiment, in other embodiments, the boss may be spaced apart from the window (e.g., along the direction of travel). While a boss 126 is configured to direct soil around each window 128 in the illustrated embodiment, in other embodiments, at least one boss may be omitted (e.g., such that soil is not directed around the respective window(s)). Furthermore, while the bosses 126 are configured to direct soil around windows 128 in the illustrated embodiment, in other embodiments, at least one boss may be configured to direct soil around another suitable portion of the respective optical soil monitoring sensor(s) (e.g., alone or in combination with the window), such as a body of the respective optical soil monitoring sensor(s). In addition, in certain embodiments, the window of at least one optical soil monitoring sensor may be substantially flush with the lateral side (e.g., the first lateral side) of the shank. In such embodiments, the respective boss may be omitted.

In certain embodiments, the soil monitoring system 102 may include one or more second optical soil monitoring sensors 130 coupled to a second lateral side 132 of the shank 104, opposite the first lateral side 121. In such embodiments, each second optical soil monitoring sensor may be configured to output respective second sensor signals indicative of one or more soil properties. In addition, the controller 114 may be communicatively coupled to the second optical soil monitoring sensor(s) 130 (e.g., via the sensor connection 122). The controller 114 may be configured to receive the second sensor signals from each second optical soil monitoring sensor 130 while the second optical soil monitoring sensor is at respective depths within the soil, and the controller 114 may be configured to determine the vertical profile(s) of the soil property/properties based on the sensor signals from the first optical soil monitoring sensor(s) 112 and the second sensor signals from the second optical soil monitoring sensor(s) 130. The soil monitoring system 102 may include any suitable number of second optical soil monitoring sensors 130 (e.g., 0, 1, 2, 3, 4, 5, 6, or more). Furthermore, any of the variations (e.g., with regard to window configuration, sensor type, etc.) disclosed above with regard to the first optical soil monitoring sensor(s) 112 may apply to the second optical soil monitoring sensor(s) 130. In addition, at least one boss may extend from the second lateral side 132 of the shank 104 to direct soil around a portion (e.g., window) of each respective second optical soil monitoring sensor. The boss(es) may have any of the configurations disclosed above with regard to the boss(es) 126 extending from the first lateral side 121 of the shank 104.

In the illustrated embodiment, the soil monitoring system 102 includes a second soil monitoring sensor 134 coupled to the shank 104 (e.g., to the first lateral side 121 of the shank 104, to the second lateral side 132 of the shank 104, to a front side of the shank 104, or to a rear side of the shank 104, etc.), in which the second soil monitoring sensor 134 is not an optical sensor. The second soil monitoring sensor 134 is communicatively coupled to the controller 114 (e.g., via the sensor connection 122), and the second soil monitoring sensor 134 is configured to output a sensor signal (e.g., second sensor signal) indicative of a respective soil property. In certain embodiments, the controller may determine the vertical profile(s) of the soil property/properties based on the respective sensor signal(s) from the optical soil monitoring sensor(s) and the sensor signal from the second soil monitoring sensor. The second soil monitoring sensor may include any suitable type(s) of non-optical soil monitoring sensor(s), such as conductivity sensor(s), radio frequency sensor(s), ultrasonic sensor(s), other suitable type(s) of sensor(s), or a combination thereof. While the soil monitoring system 102 includes a single second soil monitoring sensor 134 in the illustrated embodiment, in other embodiments, the soil monitoring system may include more or fewer second soil monitoring sensors (e.g., 0, 2, 3, 4, or more). For example, in certain embodiments, the second soil monitoring sensor may be omitted.

As previously discussed, the controller 114 is configured to determine vertical profile(s) of the soil property/properties based on the sensor signals from the soil monitoring sensor(s). Furthermore, in certain embodiments, the controller 114 is configured to determine the soil property/properties at a depth beneath the maximum depth of the optical soil monitoring sensor(s). For example, the controller may receive a first sensor signal indicative of the soil property/properties at a first depth (e.g., from one optical soil monitoring sensor, from a single optical soil monitoring sensor, etc.) and a second sensor signal indicative of the soil property/properties at a second depth (e.g., from another optical soil monitoring sensor, from the single optical soil monitoring sensor, etc.). In addition, the controller may determine the soil property/properties at a third depth (e.g., beneath the first and second depths) based on the soil property/properties at the first depth and the soil property/properties at the second depth. For example, in certain embodiments, the soil property/properties may include the nitrate-N concentration/level within the soil. In such embodiments, the controller may utilize the late spring nitrate test (LSNT) formula/pre-sidedress nitrate test (PSNT) formula and/or the pre-plant nitrate test (PPNT) formula to determine the nitrate-N concentration/level within the soil at a third depth based on the nitrate-N concentration/level at the first and second depths. For example, the first depth may be within 0-12 inches (e.g., within 0-30 cm) or within 0-24 inches (e.g., within 0-60 cm), the second depth may be within 0-12 inches (e.g., within 0-30 cm) or within 0-24 inches (e.g., within 0-60 cm), and the third depth may be about 24-36 inches (e.g., about 60-90 cm). The first sensor signal indicative of the soil property/properties at the first depth and the second sensor signal indicative of the soil property/properties at the second depth may be received from a single optical soil monitoring sensor while the optical soil monitoring sensor is position at the first depth and the second depth, or the first sensor signal indicative of the soil property/properties at the first depth and the second sensor signal indicative of the soil property/properties at the second depth may be received from different optical soil monitoring sensors (e.g., mounted on the same shank 104 or on different shanks).

While utilizing the nitrate-N concentration/level at two depths to determine the nitrate-N concentration/level at a third depth is disclosed above, in certain embodiments, the controller may be configured to determine the nitrate-N concentration/level at a depth beneath the maximum depth of the optical soil monitoring sensor(s) based on the nitrate-N concentrations/levels at more than two depths. For example, in certain embodiments, the controller may receive a first sensor signal indicative of the nitrate-N concentration/level at a first depth (e.g., within 0-12 inches/0-30 cm), a second sensor signal indicative of the nitrate-N concentration/level at a second depth (e.g., within 0-12 inches/0-30 cm), a third sensor signal indicative of the nitrate-N concentration/level at a third depth (e.g., within 12-24 inches/30-60 cm), and a fourth sensor signal indicative of the nitrate-N concentration/level at a fourth depth (e.g., within 12-24 inches/30-60 cm). In such embodiments, the controller may determine the nitrate-N concentration/level at a fifth depth (e.g., 24-36 inches/60-90 cm) based on the nitrate-N concentrations/levels at the first, second, third, and fourth depths. Furthermore, while the nitrate-N concentration/level and the LSNT, PSNT, and PPNT formulas are disclosed above, in certain embodiments, the controller may determine any suitable soil property/properties (e.g., soil density, soil moisture content, organic composition, etc.) at the third depth based on the soil properties at the first and second depths using any suitable technique(s), such as linear extrapolation, quadratic extrapolation, etc. In addition, in certain embodiments, the controller may be configured to determine the soil property/properties at a depth beneath the maximum depth of the optical soil monitoring sensor(s) based on measurements of soil property/properties at different times (e.g., at the same depth, at different depths, at multiple depths during at least one time, etc.). For example, the soil monitoring system may be configured to monitor the soil property/properties before and after application of nitrogen fertilizer.

In the illustrated embodiment, the soil monitoring system 102 includes a user interface 136 communicatively coupled to the controller 114. The user interface 136 is configured to receive input from an operator and to provide information to the operator. The user interface 136 may include any suitable input device(s) for receiving input, such as a keyboard, a mouse, button(s), switch(es), knob(s), other suitable input device(s), or a combination thereof. In addition, the user interface 136 may include any suitable output device(s) for presenting information to the operator, such as a speaker, indicator light(s), other suitable output device(s), or a combination thereof. In the illustrated embodiment, the user interface 136 includes a display 138 configured to present visual information to the operator. In certain embodiments, the display 138 may include a touchscreen interface configured to receive input from the operator.

As previously discussed, the controller 114 is configured to determine vertical profile(s) of soil property/properties based on sensor signals indicative of the soil property/properties. In certain embodiments, the controller 114 may instruct the display 138 of the user interface 136 to present a visual indication of the vertical profile(s) to the operator, thereby enabling the operator to control operation of the agricultural implement based on the vertical profile(s). Furthermore, in certain embodiments, the controller 114 may determine a variation in operation of the agricultural implement based on the vertical profile(s) of the soil property/properties. In such embodiments, the controller 114 may instruct the display 138 of the user interface 136 to present the variation to the operator (e.g., as a recommendation for controlling the agricultural implement). For example, the controller may determine a variation in nitrogen fertilizer application based on a vertical profile of nitrate-N within the soil. The controller may then instruct the display to present the variation to the operator, and the operator may control a nitrogen fertilizer application system to control the nitrogen fertilizer being applied to the soil. In certain embodiments, the controller may also determine a variation in a ground engaging tool depth, a speed of the agricultural implement, a direction of movement of the agricultural implement, other suitable operating parameter(s) of the agricultural implement, or a combination thereof, and instruct the display to present the variation(s) to the operator.

Furthermore, in certain embodiments, the controller 114 is configured to determine vertical profile(s) of the soil property/properties at multiple positions within the field to generate a set of vertical profiles. In such embodiments, the controller 114 may determine a map of the field based on the set of vertical profiles. For example, the map may include a three-dimensional representation (e.g., length, width, and depth) of the soil property/properties within the field. In certain embodiments, the controller 114 may instruct the display 138 of the user interface 136 to present the map to the operator. Furthermore, in certain embodiments, the soil monitoring system may include a communication interface configured to output data to a remote control/monitoring system. In such embodiments, the controller may instruct the communication interface to output the map, the vertical profile(s) of the soil property/properties, other suitable data, or a combination thereof, to the remote control/monitoring system.

In the illustrated embodiment, the soil monitoring system 102 includes an agricultural product application system 140 configured to output agricultural product(s) to the soil. As illustrated, the controller 114 is communicatively coupled to the agricultural product application system 140. In addition, the controller 114 is configured to control output of the agricultural product(s) based on the vertical profile(s) of the soil property/properties. For example, in certain embodiments, the agricultural product application system 140 may be configured to output nitrogen fertilizer, and the soil property/properties may include nitrate-N. In such embodiments, the controller 114 may control output of the nitrogen fertilizer from the agricultural product application system 140 based on the vertical profile(s) of the nitrate-N concentration/level. For example, the controller 114 may compare the vertical profile(s) of the nitrate-N concentration/level to an nitrate-N prescription map of the field, and the controller 114 may control the output of the nitrogen fertilizer based on a difference between the nitrate-N concentration/level within the vertical profile(s) and the nitrate-N concentration/level within the prescription map. Furthermore, the agricultural product application system 140 may be configured to output other suitable agricultural product(s) (e.g., alone or in combination with the nitrogen fertilizer), such as seed, other suitable fertilizer(s), other suitable agricultural product(s), or a combination thereof, and the controller may control output of the agricultural product(s) based on the vertical profile(s) of the soil property/properties (e.g., soil density, organic composition, soil moisture content, etc.). While the soil monitoring system 102 includes the agricultural product application system 140 in the illustrated embodiment, in other embodiments, the agricultural product application system may be omitted.

In the illustrated embodiment, the soil monitoring system 102 includes a ground engaging tool control system 142. The ground engaging tool control system 142 is configured to control penetration depth of one or more ground engaging tools of the agricultural implement, such as shank(s), coulter disc(s), disc blade(s), finishing disc(s), finishing reel(s), tine(s), opener disc(s), opener blade(s), other suitable type(s) of ground engaging tool(s), or a combination thereof. In the illustrated embodiment, the ground engaging tool control system 142 is communicatively coupled to the controller 114, and the controller 114 is configured to control operation of the ground engaging tool(s) via the ground engaging tool control system 142 based on the vertical profile(s) of the soil property/properties. For example, the controller 114 may instruct the ground engaging tool control system 142 to adjust a penetration depth of at least one ground engaging tool, an angle of at least one ground engaging tool relative to the direction of travel, a downforce applied by at least one ground engaging tool, other suitable property/properties of at least one ground engaging tool, or a combination thereof, based on the vertical profile(s) of the soil property/properties (e.g., nitrate-N concentration/level, soil density, organic composition, soil moisture content, etc.). While the soil monitoring system 102 includes the ground engaging tool control system 142 in the illustrated embodiment, in other embodiments, the ground engaging tool control system may be omitted.

In the illustrated embodiment, the soil monitoring system 102 includes a direction control system 144 communicatively coupled to the controller 114. The direction control system 144 may control the direction of movement of the agricultural implement (e.g., via controlling the direction of movement of the work vehicle towing the agricultural implement, via controlling the direction of movement of the agricultural implement relative to the tow vehicle, via controlling the direction of movement of a self-propelled agricultural implement, etc.). For example, the direction control system 144 may include a wheel angle control system, a differential braking system, a torque vectoring system, an articulated steering system, or a combination thereof. The controller 114 is configured to control a direction of movement of the agricultural implement via the direction control system 144 based on the vertical profile(s) of the soil property/properties (e.g., nitrate-N concentration/level, soil density, organic composition, soil moisture content, etc.). While the soil monitoring system 102 includes the direction control system 144 in the illustrated embodiment, in other embodiments, the direction control system may be omitted.

In the illustrated embodiment, the soil monitoring system 102 includes a speed control system 146 communicatively coupled to the controller 114. The speed control system 146 may control the speed of the agricultural implement along the direction of travel (e.g., by controlling the speed of the tow vehicle, by controlling the speed of a self-propelled agricultural implement, etc.). For example, the speed control system 146 may include an engine output control system, a transmission control system, a braking control system, an electric motor controller for an electric motor, or a combination thereof. The controller 114 is configured to control a speed of the agricultural implement via the speed control system 146 based on the vertical profile(s) of the soil property/properties (e.g., nitrate-N concentration/level, soil density, organic composition, soil moisture content, etc.). While the soil monitoring system 102 includes the speed control system 146 in the illustrated embodiment, in other embodiments, the speed control system may be omitted.

While the soil monitoring system 102 includes optical soil monitoring sensor(s) 112 in the illustrated embodiment, in other embodiments, the soil monitoring system may include other suitable soil monitoring sensor(s) (e.g., alone or in combination with the optical soil monitoring sensor(s) 112 and/or the second soil monitoring sensor 134). For example, in certain embodiments, the soil monitoring system may include one or more active electromagnetic sensors configured to emit electromagnetic radiation into the soil within the probing area and to receive electromagnetic radiation from the soil within the probing area. The electromagnetic radiation may be within any suitable portion of the electromagnetic spectrum, such as radio frequency radiation, microwave radiation, infrared radiation, ultraviolet radiation, visible light, other suitable electromagnetic radiation, or a combination thereof. Furthermore, in certain embodiments, the soil monitoring system may include one or more passive electromagnetic sensors configured to receive electromagnetic radiation from the soil within the probing area without emitting electromagnetic radiation into the soil within the probing area. Additionally or alternatively, the soil monitoring system may include other suitable type(s) of soil monitoring sensor(s), such as electrical conductivity sensor(s), electrostatic sensor(s), capacitance sensor(s), inductive sensor(s), other suitable type(s) of sensor(s), or a combination thereof.

Figure 6:
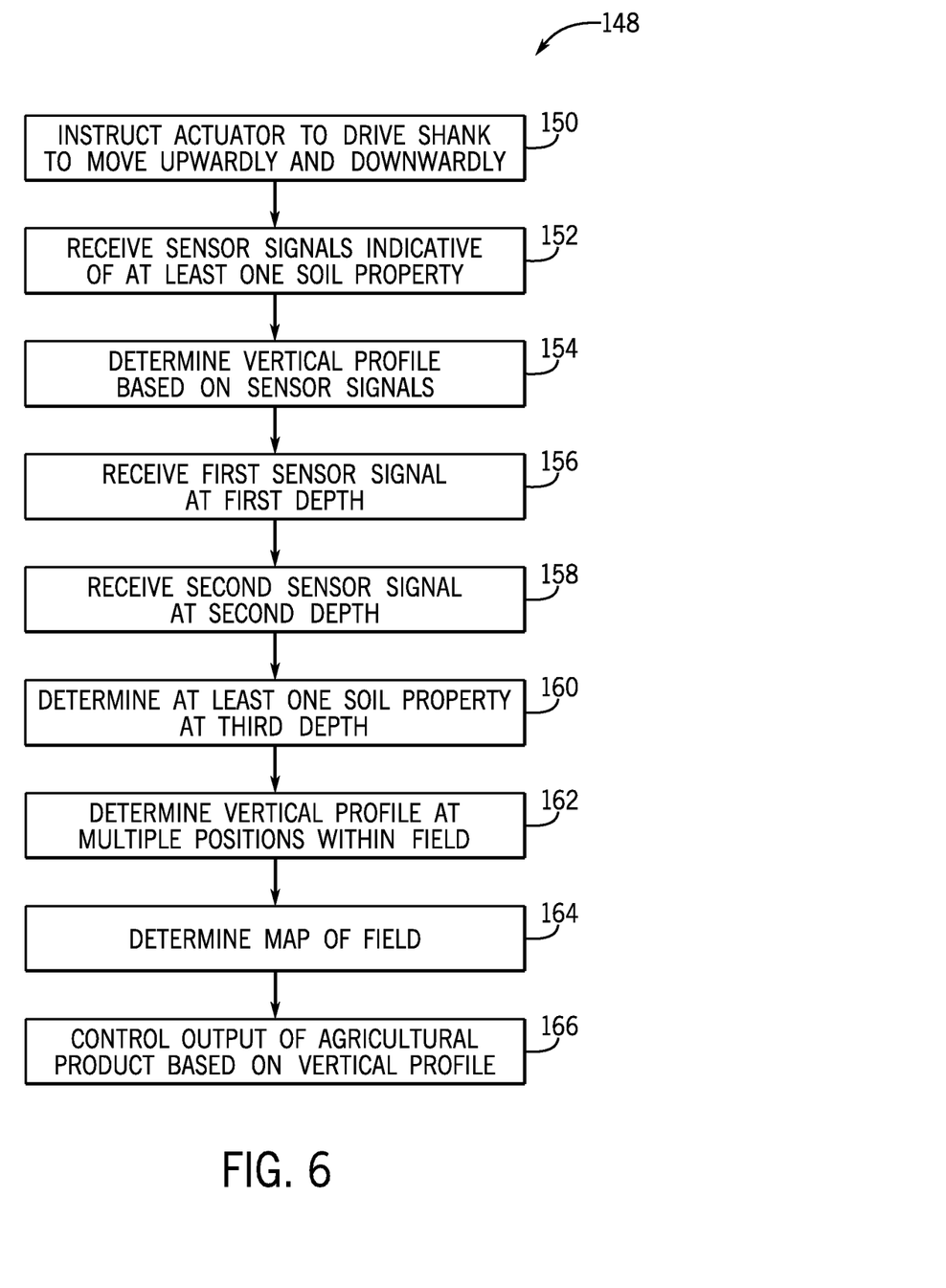
FIG. 6 is a flow diagram of an embodiment of a method for monitoring soil.

FIG. 6 is a flow diagram of an embodiment of a method 148 for monitoring soil. First, as represented by block 150, an actuator is instructed to drive a shank to move upwardly and downwardly, such that at least one soil monitoring sensor (e.g., at least one optical soil monitoring sensor) coupled to a lateral side of the shank moves in a cyclical pattern through soil as the shank is driven to move through the soil along a direction of travel. As previously discussed, the actuator may include any suitable type(s) of actuator(s), such as hydraulic actuator(s), pneumatic actuator(s), electromechanical actuator(s), other suitable type(s) of actuator(s), or a combination thereof. Next, sensor signals from the at least one soil monitoring sensor are received while the at least one soil monitoring sensor is at respective depths within the soil, as represented by block 152. As previously discussed, each sensor signal is indicative of at least one soil property. Furthermore, in certain embodiments, the at least one soil monitoring sensor may include an optical nitrate-N sensor. As represented by block 154, a vertical profile of the at least one soil property is determined.

In certain embodiments, a first sensor signal indicative of the at least one soil property at a first depth of the respective depths is received, as represented by block 156. In addition, a second sensor signal indicative of the at least one soil property at a second depth of the respective depths is received, as represented by block 158. Next, as represented by block 160, the at least one soil property at a third depth is determined based on the at least one soil property at the first depth and the at least one soil property at the second depth. As previously discussed, the at least one soil property at the third depth may be determined using the LSNT/PSNT formula (e.g., in embodiments in which the at least one soil property includes nitrate-N), the PPNT formula (e.g., in embodiments in which the at least one soil property includes nitrate-N), or another suitable technique, such as extrapolation.

Furthermore, in certain embodiments, the vertical profile of the at least one soil property is determined at multiple positions within the field to generate multiple vertical profiles, as represented by block 162. Next, as represented by block 164, a map of the field is determined based on the multiple vertical profiles. In certain embodiments, the map includes a three-dimensional representation (e.g., length, width, and depth) of the soil property/properties within the field. In addition, in certain embodiments, the map may be presented to an operator via a display of a user interface.

In certain embodiments, as represented by block 166, output of at least one agricultural product is controlled based on the vertical profile of the at least one soil property. For example, in certain embodiments, an agricultural product application system may be configured to output nitrogen fertilizer, and the at least one soil property may include nitrate-N. In such embodiments, the output of the nitrogen fertilizer from the agricultural product application system may be controlled based on the vertical profile of the nitrate-N concentration/level. Furthermore, in certain embodiments, a ground engaging tool coupled to the agricultural implement, a speed of the agricultural implement, a direction of movement of the agricultural implement, or a combination thereof, may be controlled based on the vertical profile of the at least one soil property.

The steps of the method 148 may be performed in the order disclosed herein or in any other suitable order. In addition, in certain embodiments, the method 148 is performed by the controller of the soil monitoring system. However, in other embodiments, the method 148 may be performed by any other suitable controller or combination of controllers (e.g., including the controller of the soil monitoring system).

While only certain features have been illustrated and described herein, many modifications and changes will occur to those skilled in the art. It is, therefore, to be understood that the appended claims are intended to cover all such modifications and changes as fall within the true spirit of the disclosure.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. A soil monitoring system, comprising:
a controller comprising a memory and a processor, wherein the controller is configured to:
instruct an actuator to drive a shank to move upwardly and downwardly, such that at least one soil monitoring sensor coupled to a lateral side of the shank moves in a cyclical pattern through soil as the shank is driven to move through the soil along a direction of travel;
receive a plurality of sensor signals from the at least one soil monitoring sensor while the at least one soil monitoring sensor is at a respective plurality of depths within the soil, wherein each sensor signal of the plurality of sensor signals is indicative of at least one soil property; and
determine a vertical profile of the at least one soil property based on the plurality of sensor signals.

2. The soil monitoring system of claim 1, wherein the controller is configured to control output of at least one agricultural product based on the vertical profile of the at least one soil property.

3. The soil monitoring system of claim 1, wherein the at least one soil monitoring sensor comprises an optical nitrate-N sensor.

4. The soil monitoring system of claim 1, wherein the controller is configured to receive a first sensor signal of the plurality of sensor signals indicative of the at least one soil property at a first depth of the respective plurality of depths, to receive a second sensor signal of the plurality of sensor signals indicative of the at least one soil property at a second depth of the respective plurality of depths, and to determine the at least one soil property at a third depth based on the at least one soil property at the first depth and the at least one soil property at the second depth.

5. The soil monitoring system of claim 1, wherein the controller is configured to determine the vertical profile of the at least one soil property at multiple positions within the field to generate a plurality of vertical profiles, and the controller is configured to determine a map of the field based on the plurality of vertical profiles.

6. The soil monitoring system of claim 1, wherein the controller is configured to control operation of a ground engaging tool coupled to an agricultural implement supporting the shank, control a speed of the agricultural implement supporting the shank, control a direction of movement of the agricultural implement supporting the shank, or a combination thereof, based on the vertical profile of the at least one soil property.

7. A soil monitoring system, comprising:
a shank configured to engage soil;
an actuator coupled to the shank and configured to drive the shank to move upwardly and downwardly;
at least one soil monitoring sensor coupled to a lateral side of the shank, wherein the at least one soil monitoring sensor is configured to output a plurality of sensor signals indicative of at least one soil property; and
a controller communicatively coupled to the actuator and to the at least one soil monitoring sensor, wherein the controller comprises a memory and a processor, and the controller is configured to:
instruct the actuator to drive the shank to move upwardly and downwardly, such that the at least one soil monitoring sensor moves in a cyclical pattern through the soil as the shank is driven to move through the soil along a direction of travel;
receive the plurality of sensor signals from the at least one soil monitoring sensor while the at least one soil monitoring sensor is at a respective plurality of depths within the soil; and
determine a vertical profile of the at least one soil property based on the plurality of sensor signals.

8. The soil monitoring system of claim 7, comprising an agricultural product application system configured to output at least one agricultural product to the soil, wherein the controller is communicatively coupled to the agricultural product application system, and the controller is configured to control output of the at least one agricultural product based on the vertical profile of the at least one soil property.

9. The soil monitoring system of claim 7, wherein the at least one soil monitoring sensor comprises an optical nitrate-N sensor.

10. The soil monitoring system of claim 7, wherein the controller is configured to receive a first sensor signal of the plurality of sensor signals indicative of the at least one soil property at a first depth of the respective plurality of depths, to receive a second sensor signal of the plurality of sensor signals indicative of the at least one soil property at a second depth of the respective plurality of depths, and to determine the at least one soil property at a third depth based on the at least one soil property at the first depth and the at least one soil property at the second depth.

11. The soil monitoring system of claim 7, comprising a boss extending from the lateral side of the shank and at least partially surrounding a portion of the at least one soil monitoring sensor, wherein the boss is configured to direct soil around at least the portion of the at least one soil monitoring sensor.

12. The soil monitoring system of claim 7, comprising a closing assembly configured to close a trench formed by the shank.

13. The soil monitoring system of claim 7, wherein the at least one soil monitoring sensor comprises a plurality of soil monitoring sensors disposed along a vertical extent of the shank.

14. The soil monitoring system of claim 7, comprising at least one second soil monitoring sensor coupled to a second lateral side of the shank, opposite the lateral side of the shank, wherein the at least one second soil monitoring sensor is configured to output a plurality of second sensor signals indicative of the at least one soil property, the controller is communicatively coupled to the at least one second soil monitoring sensor, the controller is configured to receive the plurality of second sensor signals from the at least one second soil monitoring sensor while the at least one second soil monitoring sensor is at a respective plurality of second depths within the soil, and the controller is configured to determine the vertical profile of the at least one soil property based on the plurality of sensor signals and the plurality of second sensor signals.

15. The soil monitoring system of claim 7, wherein the at least one soil monitoring sensor comprises an optical soil monitoring sensor.

16. A method for monitoring soil, comprising:
instructing, via a controller comprising a memory and a processor, an actuator to drive a shank to move upwardly and downwardly, such that at least one soil monitoring sensor coupled to a lateral side of the shank moves in a cyclical pattern through soil as the shank is driven to move through the soil along a direction of travel;
receiving, via the controller, a plurality of sensor signals from the at least one soil monitoring sensor while the at least one soil monitoring sensor is at a respective plurality of depths within the soil, wherein each sensor signal of the plurality of sensor signals is indicative of at least one soil property; and
determining, via the controller, a vertical profile of the at least one soil property based on the plurality of sensor signals.

17. The method of claim 16, comprising controlling, via the controller, output of at least one agricultural product based on the vertical profile of the at least one soil property.

18. The method of claim 16, wherein the at least one soil monitoring sensor comprises an optical nitrate-N sensor.

19. The method of claim 16, comprising:
receiving, via the controller, a first sensor signal of the plurality of sensor signals indicative of the at least one soil property at a first depth of the respective plurality of depths;
receiving, via the controller, a second sensor signal of the plurality of sensor signals indicative of the at least one soil property at a second depth of the respective plurality of depths; and
determining, via the controller, the at least one soil property at a third depth based on the at least one soil property at the first depth and the at least one soil property at the second depth.

20. The method of claim 16, comprising:
  determining, via the controller, the vertical profile of the at least one soil property at multiple positions within the field to generate a plurality of vertical profiles; and
  determining, via the controller, a map of the field based on the plurality of vertical profiles.

\* \* \* \* \*